(12) United States Patent
Bryzek et al.

(10) Patent No.: US 11,571,557 B2
(45) Date of Patent: Feb. 7, 2023

(54) NASAL ORAL CARE ANTISEPTICS CLEANSING KIT

(71) Applicant: Medline Industries, LP, Northfield, IL (US)

(72) Inventors: Joseph Bryzek, Kenosha, WI (US); Sharbel Maalouf, Pleasant Prairie, WI (US); David Russo, Glenview, IL (US); Dirk Benson, Lake Forest, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 17/739,828

(22) Filed: May 9, 2022

(65) Prior Publication Data

US 2022/0265980 A1 Aug. 25, 2022

Related U.S. Application Data

(62) Division of application No. 16/171,092, filed on Oct. 25, 2018, now abandoned.

(60) Provisional application No. 62/579,004, filed on Oct. 30, 2017.

(51) Int. Cl.

| A61F 13/40 | (2006.01) |
|---|---|
| A01N 47/44 | (2006.01) |
| A61J 7/00 | (2006.01) |
| A46B 9/04 | (2006.01) |
| A46B 17/04 | (2006.01) |

(52) U.S. Cl.
CPC .......... *A61M 35/006* (2013.01); *A01N 47/44* (2013.01); *A46B 9/04* (2013.01); *A46B 17/04* (2013.01); *A61J 7/0046* (2013.01); *A46B 2200/1066* (2013.01); *A61M 2205/0205* (2013.01); *A61M 2209/06* (2013.01); *A61M 2210/0618* (2013.01); *A61M 2210/0625* (2013.01)

(58) Field of Classification Search
CPC ........ A61M 35/006; A61M 2205/0205; A61M 2209/06; A61M 2210/0625; A01N 47/44; A46B 9/04; A46B 17/04; A46B 2200/1066; A61J 7/0046
USPC .................................................. 206/570, 370
See application file for complete search history.

(56) References Cited

U.S. PATENT DOCUMENTS

| 4,828,113 A * | 5/1989 | Friedland ............... A61B 90/90 206/570 |
|---|---|---|
| 5,979,658 A * | 11/1999 | Allen ...................... A61F 17/00 206/229 |
| 7,458,464 B1 * | 12/2008 | Kutsch ............... A46B 15/0091 206/581 |
| 7,967,145 B2 * | 6/2011 | Tchouangang ....... A61C 19/066 206/570 |
| 8,181,786 B1 * | 5/2012 | Alas ..................... B65D 77/003 206/570 |
| 2008/0308450 A1 * | 12/2008 | Tchouangang ....... A61C 19/066 206/570 |

(Continued)

*Primary Examiner* — Jacob K Ackun
(74) *Attorney, Agent, or Firm* — Fitch, Even, Tabin & Flannery LLP

(57) ABSTRACT

A patient cleaning kit having a package; an insert within the package, the insert and the package forming a first cavity and a second cavity; a cover coupled to the package, the cover and the package together enveloping the insert; a premoistened nasal swab within the first cavity; an oral swab within the second cavity; a toothbrush within the second cavity; and a bottle of germicidal solution within the package.

8 Claims, 14 Drawing Sheets

(56) References Cited

U.S. PATENT DOCUMENTS

| | | | | |
|---|---|---|---|---|
| 2010/0078347 A1* | 4/2010 | Brinker | ............... | A61B 50/30 |
| | | | | 206/438 |
| 2010/0270203 A1* | 10/2010 | Khan | ............... | A61F 13/0259 |
| | | | | 206/572 |
| 2011/0293668 A1* | 12/2011 | Conover | ............... | A61P 1/02 |
| | | | | 424/49 |
| 2019/0126023 A1* | 5/2019 | Bryzek | ............... | A61F 17/00 |

* cited by examiner

NASAL ORAL CARE ANTISEPTICS CLEANSING KIT

This application is a division of U.S. application Ser. No. 16/171,092 filed Oct. 25, 2018, which claims the benefit of U.S. Provisional Application No. 62/579,004 filed Oct. 30, 2017, for NASAL ORAL CARE ANTISEPTICS CLEANSING KIT, which are incorporated in their entireties herein by reference.

TECHNICAL FIELD

The present description relates to patient hygiene, specifically patient oral and nostril hygiene for patients in a caregiver setting that are unable to perform personal cleaning activities themselves.

BACKGROUND

Patients in care facilities, such as hospitals, inpatient occupational therapy facilities, nursing homes, and the like, or in-home healthcare environments, often suffer from poor hygiene, due to difficulties in performing routine cleaning activities. Often the patient is unable to assist in these activities, and therefore such activities must be performed by caregivers working for the facilities or patients.

Heretofore cleaning of a patient's nose and mouth has been performed by a caregiver, who must assemble the needed supplies and devices, locate such supplies and devices near the patient, and manipulate the supplies and devices, so as to effect the cleaning, all the while remembering not to omit steps in the cleaning process.

It has now been found useful to provide a patient cleaning kit comprising a package; an insert within the package, the insert and the package forming a first cavity and a second cavity; a cover coupled to the package, the cover and the package together enveloping the insert; a premoistened nasal swab within the first cavity; an oral swab within the second cavity; a toothbrush within the second cavity; and a bottle of germicidal solution within the package. Also useful is a method of patient care comprising: opening a package; removing a nasal swab from a first cavity defined by the package and an insert; cleaning a first nostril of the patient with the first nasal swab; removing a nasal swab from the first cavity; cleaning a second nostril of the patient with the second nasal swab; removing a bottle of germicidal solution from the package; removing an amount of the germicidal solution from the bottle of germicidal solution; removing an oral swab from a second cavity defined by the package and the insert; dispensing a portion of the germicidal solution onto an oral swab; and cleaning a mouth of the patient with the oral swab.

DETAILED DESCRIPTION

Figure 1:
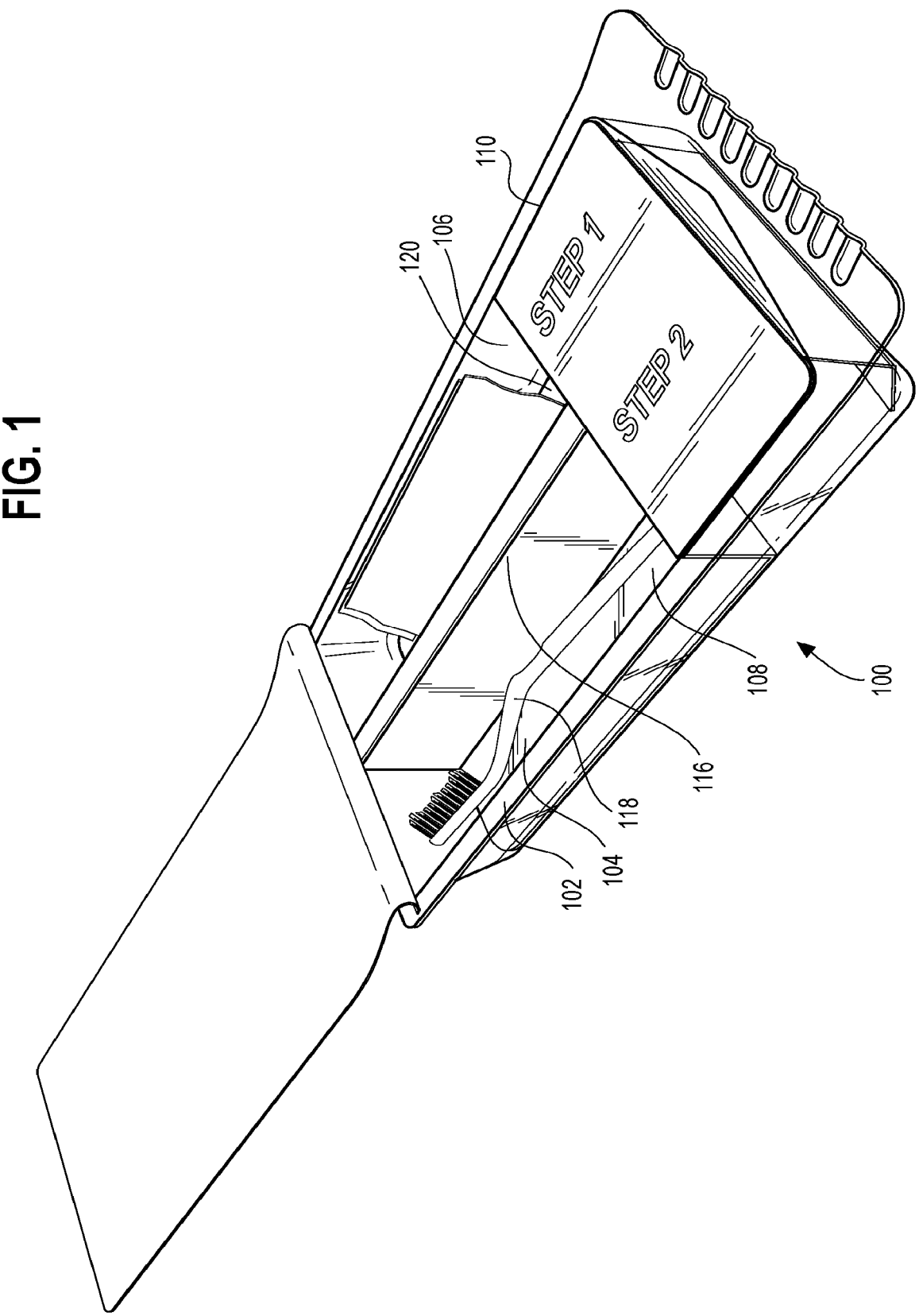
FIG. 1 is top plan view of an exemplary embodiment of a nasal and oral care antiseptic cleansing kit, shown with the cover removed.

Referring to FIG. 1, and the illustrated nasal and oral care antiseptic cleansing kit 100, shown is a package 102, which may be a blow fill seal package 102, a package insert 104, a first cavity 106 formed between the interior wall of the package 102 and the package insert 104, and a second cavity 108 formed between the interior wall of the package 102 and the package insert 104. Also shown is an instructions panel 110 and a plurality of premoistened nasal antiseptic swabs 112 (four swabs are included, but a larger or smaller number may be included). The swabs 112 are individually packaged in wrappers, which may be numbered or otherwise differentiated. For example, the swabs may be identified with an "R" or an "L," to indicate whether the premoistened nasal antiseptic swab contained therein should be used with the "right" or "left" nostril, or numbered "1" and "2" to signify that the swabs may be used first or second. The kit 100 further includes bottle 114 (shown below in FIG. 14) of chlorhexidine gluconate solution, an oral swab 116 (unpackaged, shown below in FIG. 14), a toothbrush 118, and a medicine cup 120 (shown below in FIG. 14).

The swabs 112 are positioned within the first cavity 106, and the oral swab 116, the bottle 114 of chlorhexidine gluconate, and the toothbrush 118 are packaged within the second cavity 108. The medicine cup 120 may be positioned in the second cavity 108, or may be positioned underneath the instructions panel 110 between the package insert 104 and the package 102.

The package insert 104 is positioned within a concavity 122 (or well) formed in the package 102. The insert includes vertical wall structures 124, 126 that together with the package 102 form the first cavity 106 and the second cavity 108. For example, the package insert 104 may include one or more vertical wall structures 124, 126 coupled to a fold or folds in the package insert 104 between a plane defined by an upper edge 125 of the package 102 to a base of the concavity 122 formed by the package 102.

The instructions panel 110 may graphically and/or textually indicate instructions to a caregiver for use of the contents of the first cavity 106 and the second cavity 108 (as well as a medicine cup 120, which may be positioned under the instructions panel 110). Advantageously these instructions may be positioned adjacent to the first cavity 106 and the second cavity 108 with instructions pertaining to the contents of the first cavity 106 being positioned adjacent to the first cavity 106 and instructions pertaining to the contents of the second cavity 108 being adjacent to the second cavity 108.

The package 102 is sealed with, for example, paper cover 302 (FIG. 3) that may be adhesively secured to an upper lip of the package 102. The cover may otherwise be conventional and may be removed by pulling the paper cover 302 across the upper edge 125 of the package 102 so as to partially or completely remove the paper cover 302 from the package 102.

In operation, a caregiver, for example, removes the paper cover 302 by pulling the paper cover 302 across the upper edge 125 of the package 102 so as to unseal the package 102 and remove the paper cover 302 either partially or completely from the package 102. The caregiver then observes the instructions on the instructions panel 110 and follows the instructions pertaining to the contents of the first cavity 106, and then follows instructions pertaining to the contents of the second cavity 108.

Specifically, the caregiver removes a first nasal antiseptic swab 112 (which may be labeled, for example, "1") from the first cavity 106 and opens the wrapper enveloping the first nasal antiseptic swab. Preferably, the first nasal antiseptic swab 112 is pre-moistened with, for example, povidone-iodine USP 10%. Following the instructions, the caregiver cleans the patient, by placing the nasal antiseptic swab into a first nostril of the patient, sweeping the first nasal antiseptic swab 112 around the first nostril.

Next, the caregiver removes the second nasal antiseptic swab (which may be labeled, for example "2") from the first cavity 106 and opens the wrapper enveloping the second nasal antiseptic swab. The second nasal antiseptic swab may, preferably, also be premoistened with, for example, povidone-iodine USP 10%. Following the instructions, the caregiver cleans the patient, by placing the second nasal antiseptic swab into a second nostril of the patient, sweeping the second nasal antiseptic swab around the second nostril.

Next, the caregiver removes the third nasal antiseptic swab (which may be labeled, for example, "3") from the first cavity 106, and opens the wrapper enveloping the third nasal antiseptic swab. The third nasal antiseptic swab may, preferably, also be premoistened with, for example, povidone-iodine USP 10%. Following the instructions, the caregiver cleans the patient, by placing the third nasal antiseptic swab into the first nostril of the patient, sweeping the third nasal antiseptic swab around the first nostril.

Next, the caregiver removes the fourth nasal antiseptic swab (which may be labeled, for example, "4") from the first cavity 106, and opens the wrapper enveloping the fourth nasal antiseptic swab. The fourth nasal antiseptic swab may, preferably, also be premoistened with, for example, povidone-iodine USP 10%. Following the instructions, the caregiver cleans the patient by placing the fourth nasal antiseptic swab into the second nostril of the patient, sweeping the fourth nasal antiseptic swab around the second nostril.

Next, the caregiver removes the medicine cup 120 and the chlorhexidine gluconate bottle 114 from the second cavity 108 (or in case of the medicine cup 120 optionally from below the instructions panel 110). The caregiver then pours an amount of the chlorhexidine gluconate from the bottle 114 into the medicine cup 120. This amount may be all or less than all of the contents of the bottle 114 of chlorhexidine gluconate.

The caregiver then moistens the oral swab 116 in the chlorhexidine gluconate within the medicine cup 120 and uses the oral swab 116 to cleanse the mouth (oral cavity) of the patient by sweeping the oral swab 116 across the gums and teeth of the patient.

In addition, the caregiver moistens the toothbrush 118 in the chlorhexidine gluconate solution within the medicine cup 120 and brushes the patient's teeth and gums with the toothbrush 118 moistened with the chlorhexidine gluconate.

Periodically during the cleansing of the gums with the oral swab 116 and the cleansing of the teeth and gums with toothbrush 118, the caregiver may re-moisten the oral swab 116 and/or the toothbrush 118 with the chlorhexidine gluconate from the medicine cup 120.

As needed, additional chlorhexidine gluconate may be added to the medicine cup 120 from the bottle 114 of chlorhexidine gluconate (provided the entire amount of the chlorhexidine is not transferred in the first instance into the medicine cup 120).

Figure 2:
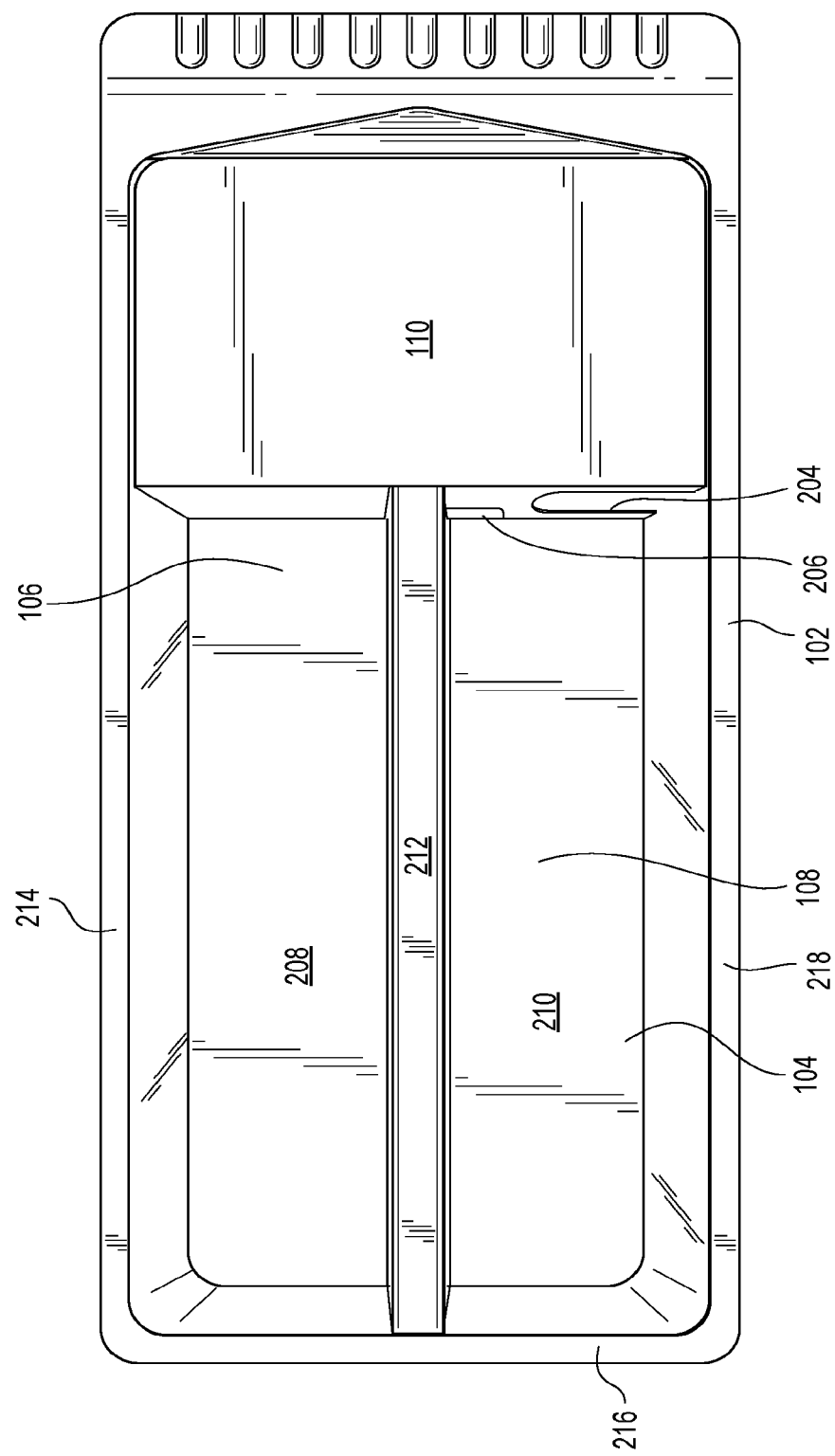
FIG. 2 is a top plan view of an exemplary embodiment, with the components of the kit removed and showing an insert.

Referring to FIG. 2, shown is the package 102 and the package insert 104, a first cavity 106 is formed between one or more dividers 212 of the package insert 104 and a first wall 214 and second wall 216 of the package 102, and a second cavity 108 is formed between the one or more dividers 212 and the second wall 216 and a third wall 218 of the package 102. Also shown is the instructions panel 110, an arcuate notch 204 for securing the bottle 114 of chlorhexidine gluconate, and a slot 206 for securing the toothbrush 118.

In accordance with the embodiment shown, the package insert 104 includes a first floor section 208 and a second floor section 210 on which the contents of the package 102 are placed. Advantageously, the first and second floor sections 208, 210 facilitate removal of the contents through the lifting of the package insert 104 from the package 102, which lifts the contents from the package 102.

Figure 3:
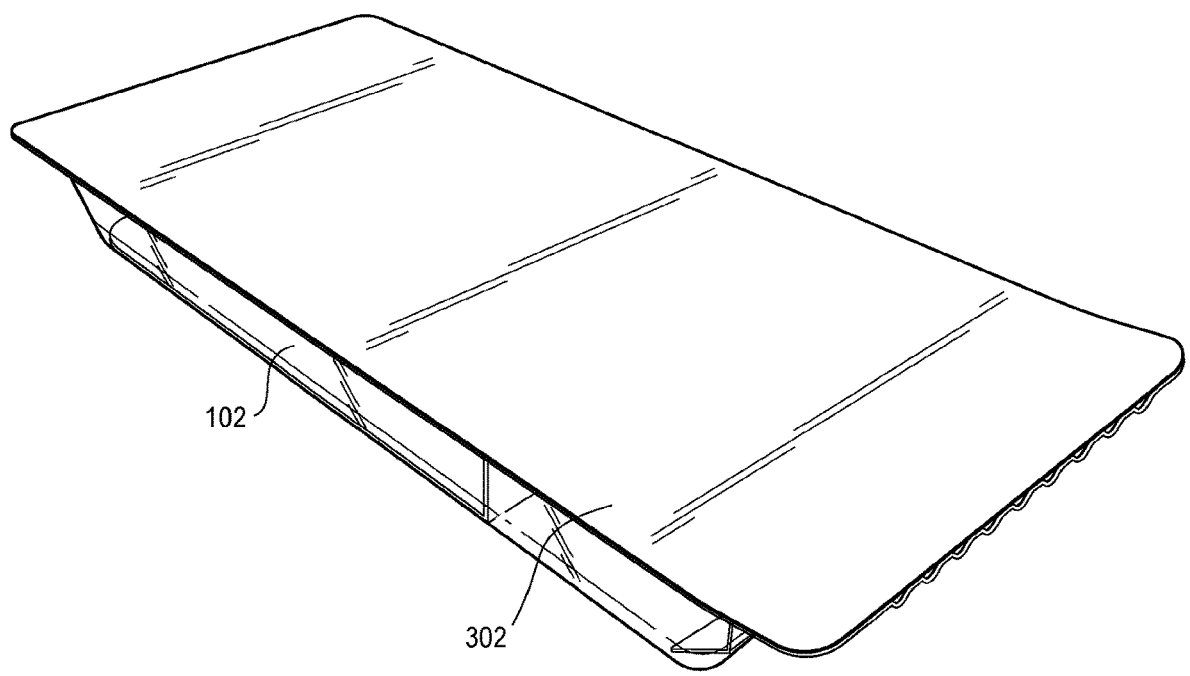
FIG. 3 is a top plan view of the kit shown in FIG. 1, shown with the outer cover affixed.
Figure 4:
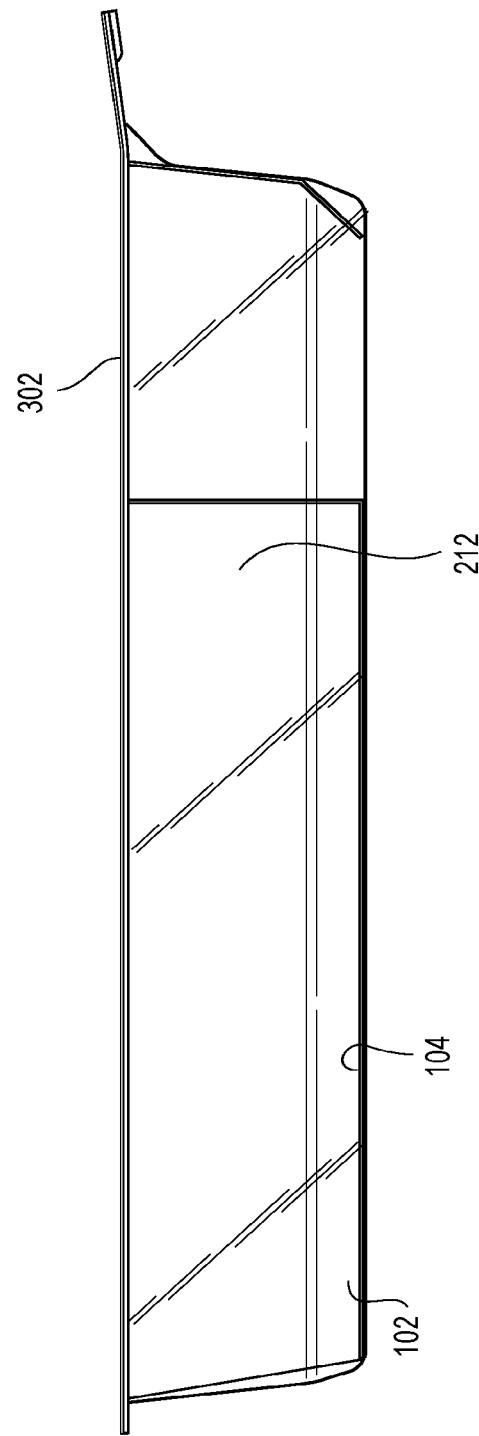
FIGS. 4 and 5 are first and second opposing side views of the kit shown in FIG. 1, each view illustrating the kit with the components removed.
Figure 5:
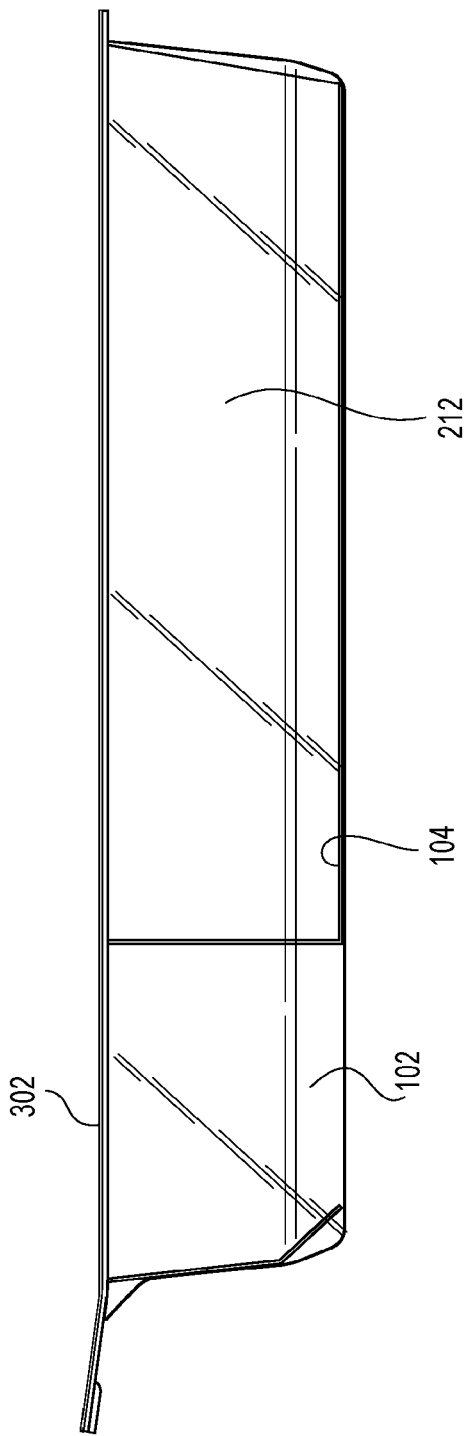
Figure 6:
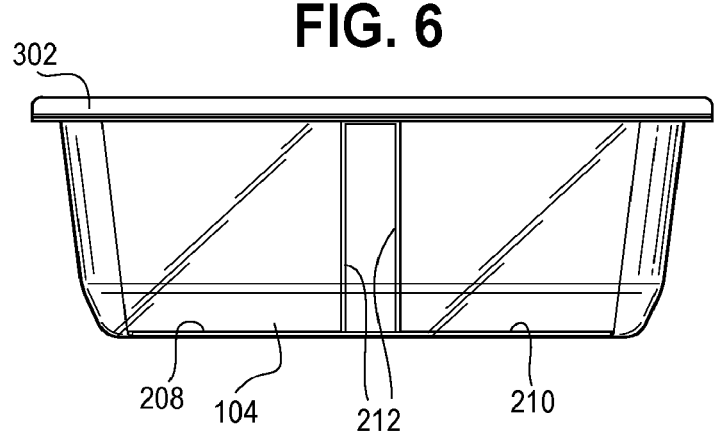
FIGS. 6 and 7 are first and second opposing end views of the kit shown in FIG. 1, each view illustrating the kit with the components removed.
Figure 7:
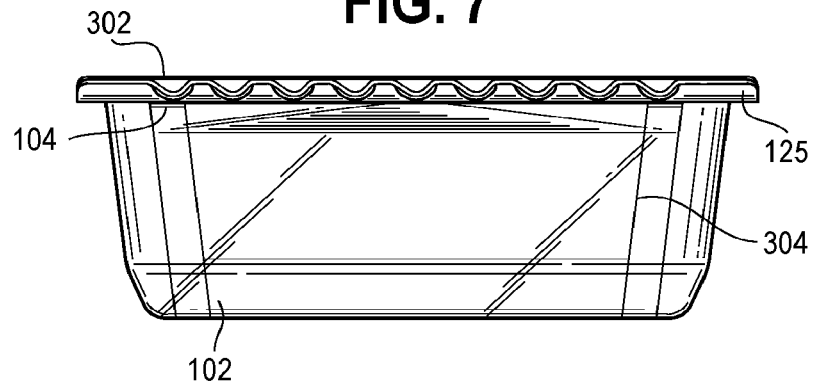

Referring to FIGS. 3-5, shown is the package 102 with the paper cover 302 in a closed position and the insert 104 (FIG. 4) and the divider 212. Referring to FIG. 6, shown is an end view of the package insert 104 with the paper cover 302 in a closed position. Shown is the divider 212, and the first floor section 208 and the second floor section 210. Referring to FIG. 7, shown is an opposite end view of the package 102 and package insert 104 with the paper cover 302 in a closed position. A support flap 304 descends from the instructions panel 110 to a bottom of the package 102. The support flap 304 prevents the instructions panel 110 from descending into the package 102 well or cavity, thereby maintaining the instructions panel 110 in a substantially coplanar arrangement with the upper edge 125 of the package 102.

Figure 8:
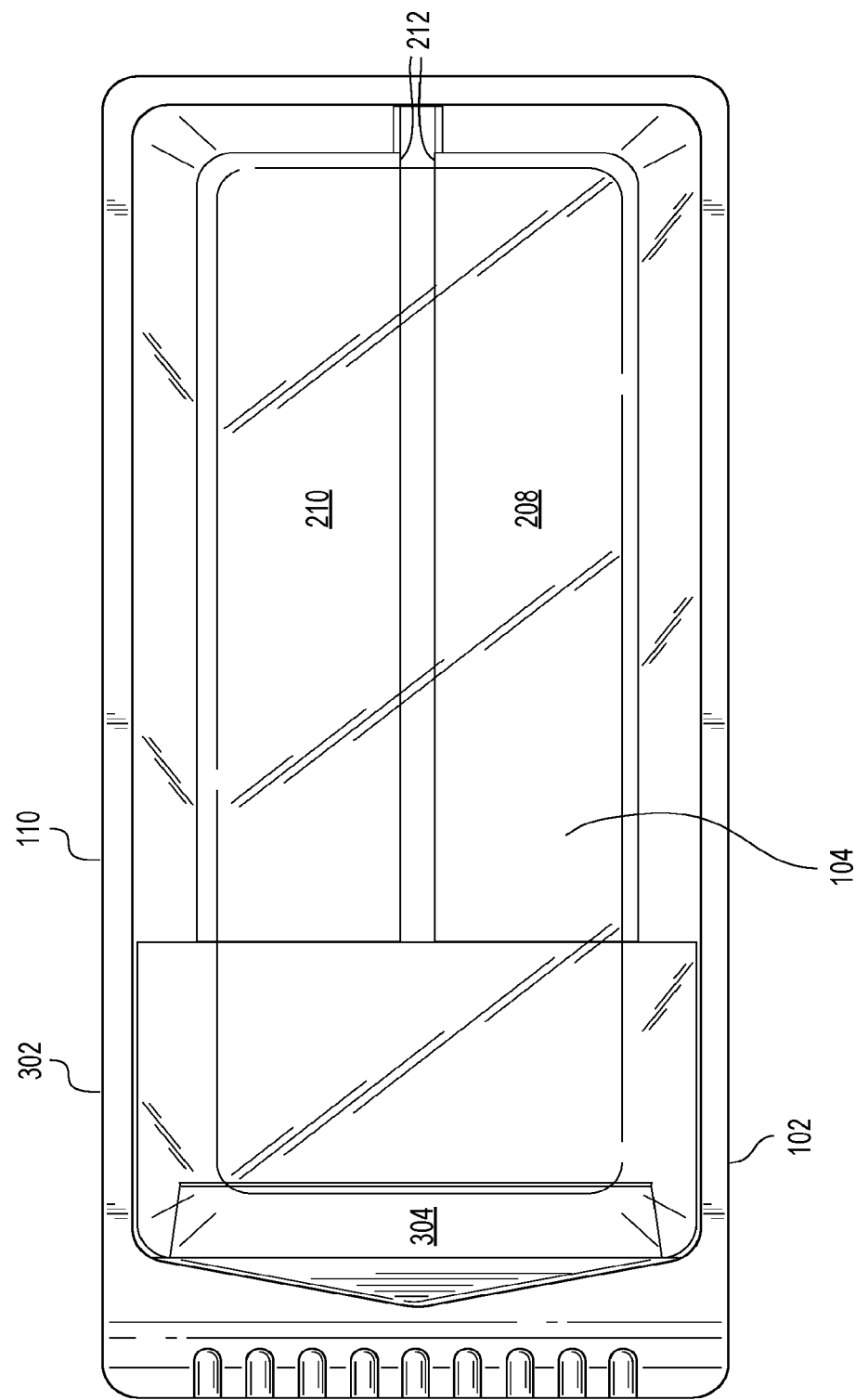
FIG. 8 is a bottom view of the kit shown in FIG. 1

Referring to FIG. 8, shown is the first floor section 208, the second floor section 210 and the one or more dividers 212. Also shown is the instructions panel 110 and the support flap 304.

Figure 9:
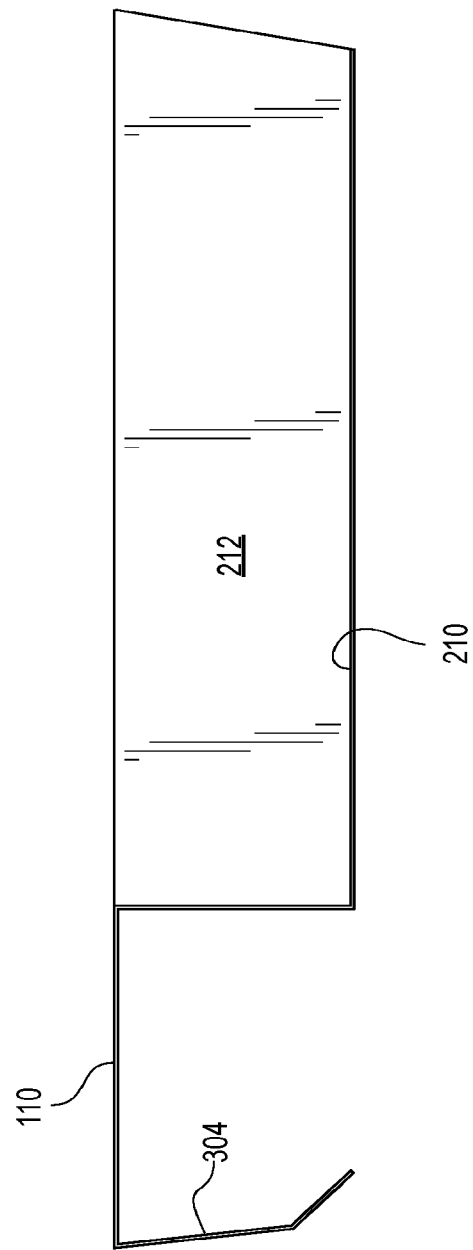
FIG. 9 is a side elevational view of the package insert of the kit shown in FIG. 1.
Figure 10:
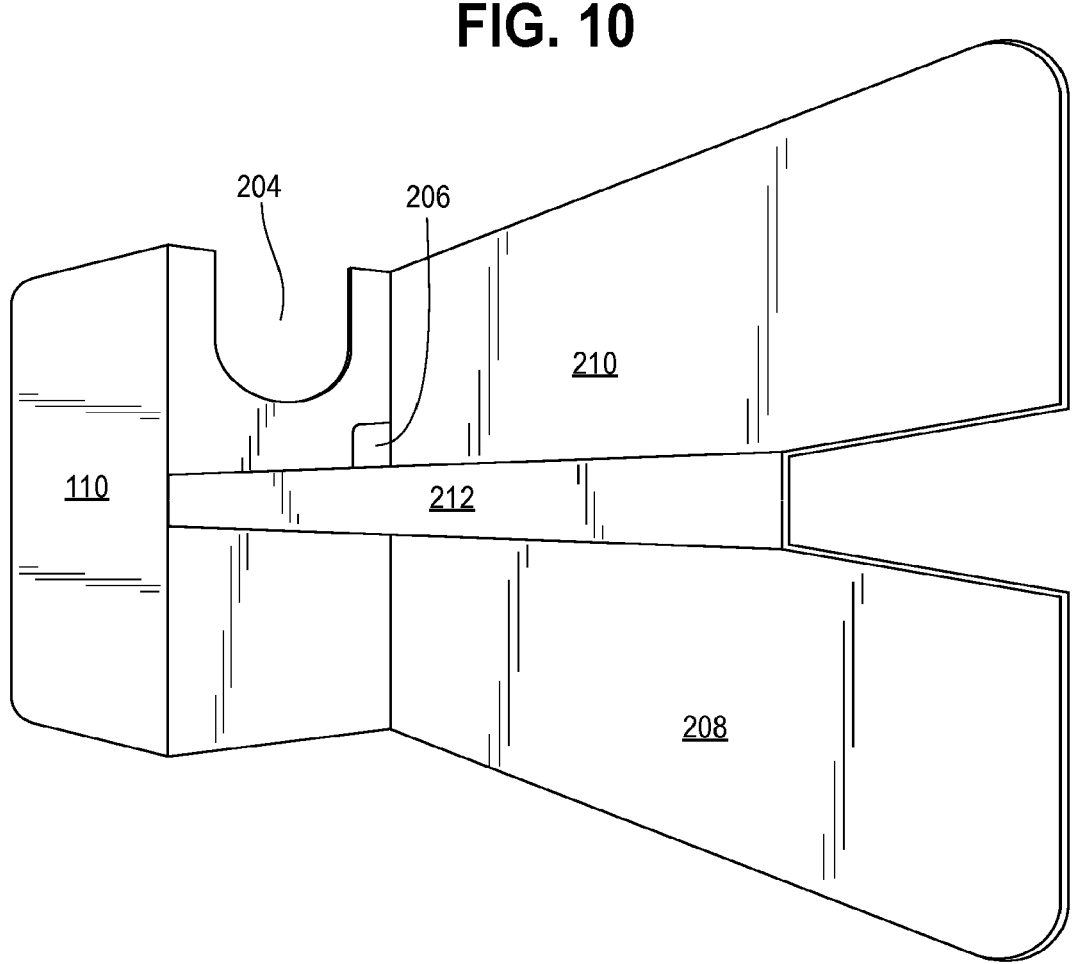
FIG. 10 is a perspective end view of the package insert shown in FIG. 9.
Figure 11:
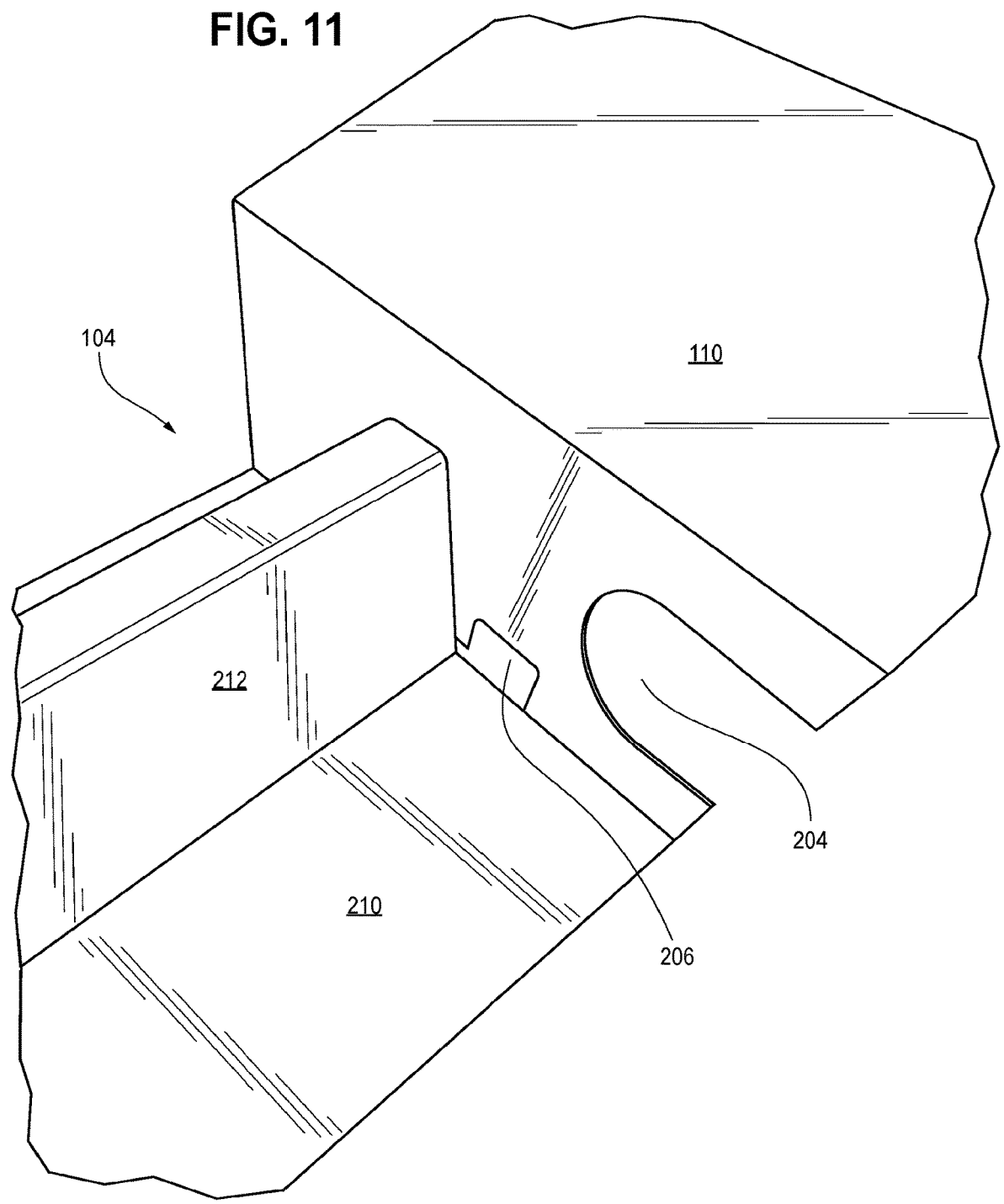
FIGS. 11 and 12 are perspective views of a portion of the package insert shown in FIG. 9.
Figure 12:
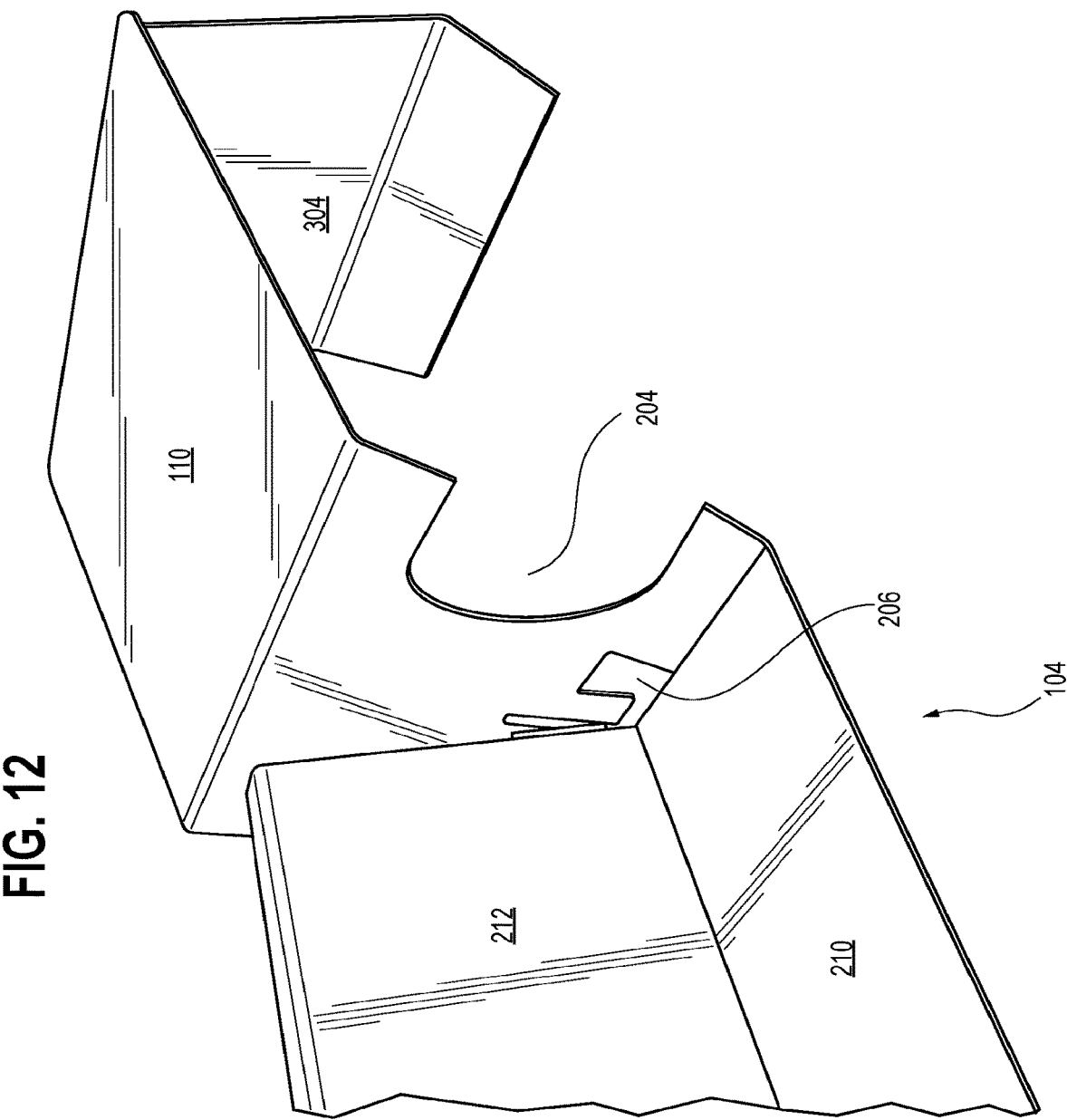

Referring to FIGS. 9 and 10, shown in FIG. 9 is the second floor section 210, the one or more dividers 212, the instructions panel 110 and the support flap 304. FIG. 10, depicts the first floor section 208, the second floor section 210, the one or more dividers 212, the instructions panel 110, the arcuate notch 204, and the slot 206. Most of these features are shown also in FIGS. 11 and 12.

Figure 13:
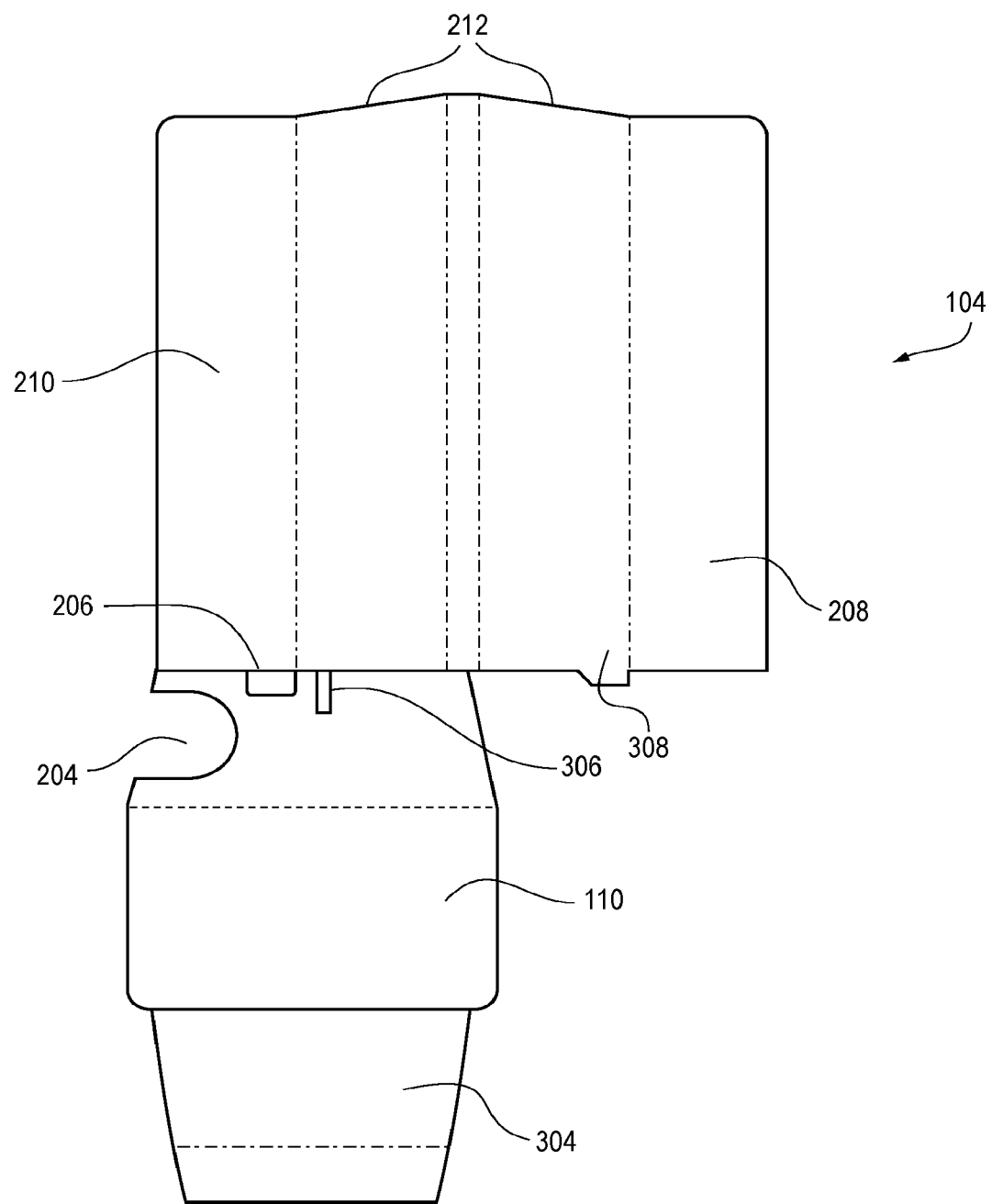
FIG. 13 is a plan view of a blank for forming the package insert illustrated in FIG. 9

Referring to the package blank shown in FIG. 13, the blank includes the first floor section 208, the second floor section 210, the one or more dividers 212, the arcuate notch 204, the slot 206, a groove 306, a tab 308, the instructions panel 110 and the support flap 304. In practice, the package insert 104 is die cut from cardstock, such as 18 pt SBS carboard, and may be folded along the dashed lines illustrated. The dashed lines may represent folds and, in addition, may represent scoring or perforation to facilitate folding. The groove 306 aligns with and receives the tab 308 when the package insert 104 is folded into the package 102. The groove 306 and the tab 308 (which are optional) cooperate to hold the package insert 104 in shape against its tendency to unfold somewhat due to the stiffness of the material.

Figure 14:
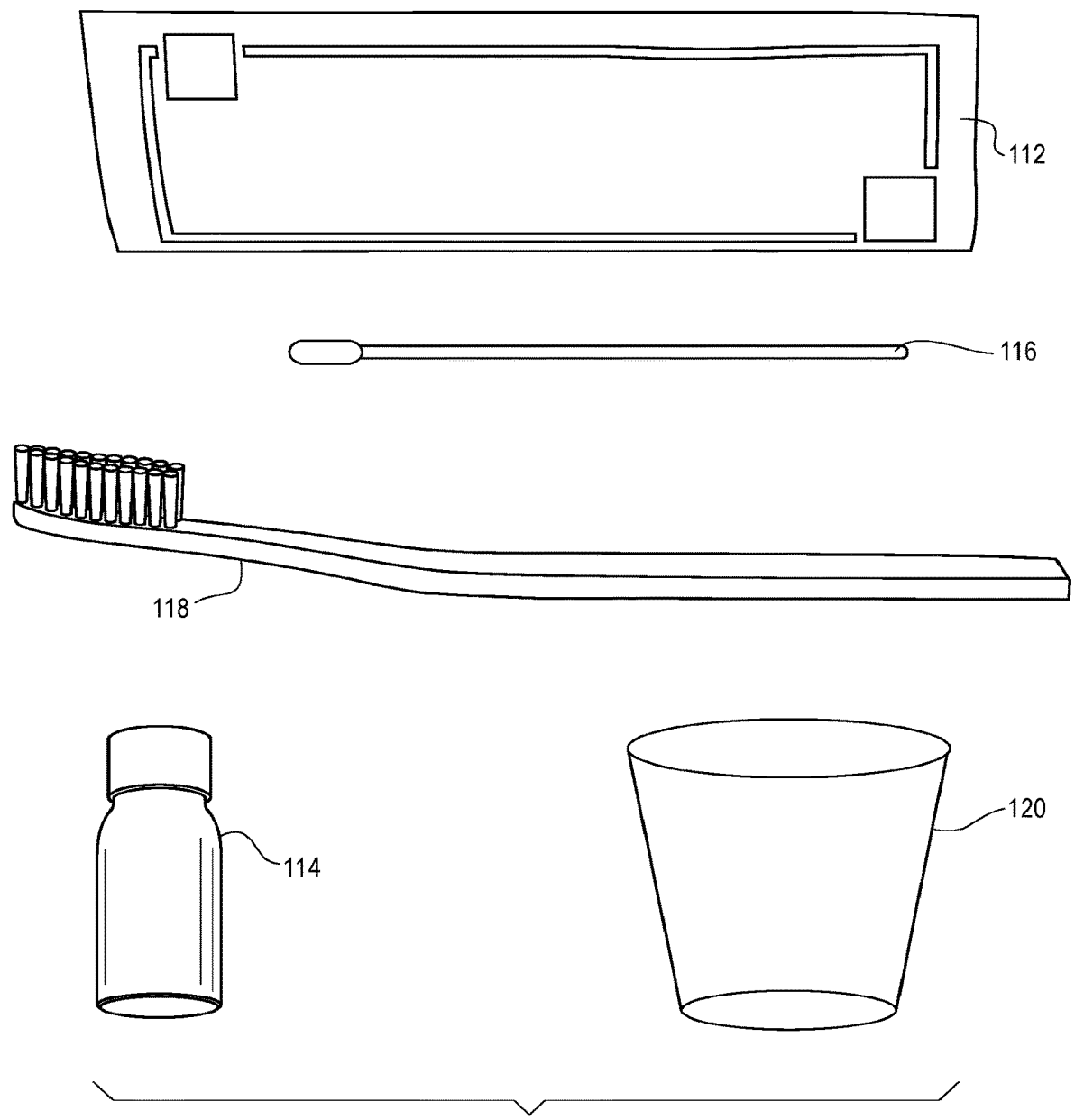
FIG. 14 is a representational view illustrating the contents of the kit shown in FIG. 1.

As represented in FIG. 14, the kit may include a plurality of individually packaged, premoistened nasal swabs 112, an oral swab 116, a toothbrush 118, a bottle 114 of chlorohexidine gluconate, and a medicine cup 120.

Figure 15:
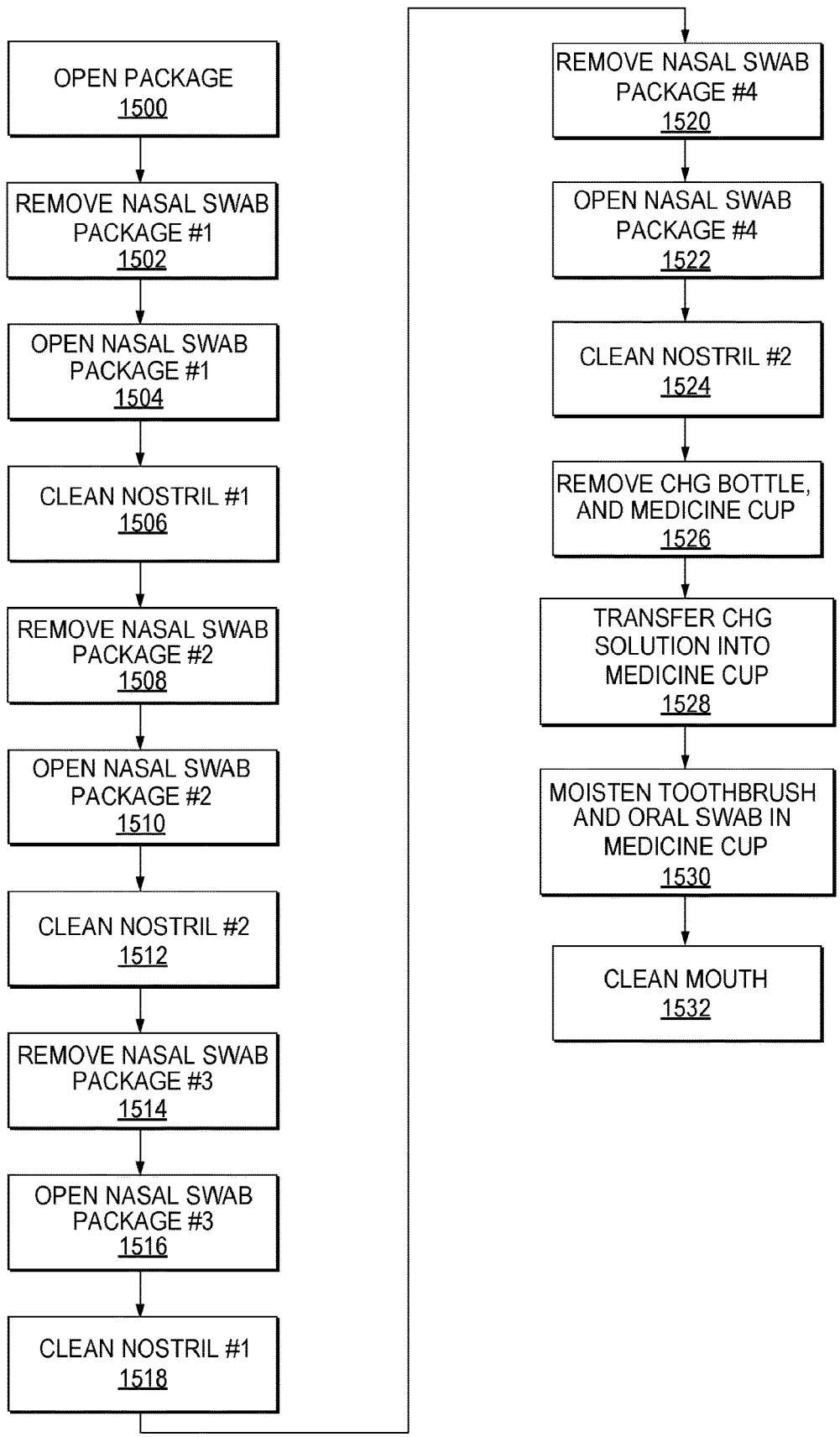
FIG. 15 is a flowchart illustrating steps in a method for using the kit shown in FIG. 1.

Referring to FIG. 15, in a first step 1500 of using the kit, a caregiver, for example, removes the paper cover 302 by pulling the paper cover 302 across the upper edge 125 of the package 102 so as to unseal the package 102 and remove the paper cover 302 either partially or completely from the package 102. The caregiver then observes the instructions on the instructions panel 110 and follows the instructions pertaining to the contents of the first cavity 106, and then follows instructions pertaining to the contents of the second cavity 108.

In a next step 1502, the caregiver removes a first nasal antiseptic swab 112 from the first cavity 106 and, in step 1504, opens the wrapper enveloping the first nasal antiseptic swab. Preferably, the first nasal antiseptic swab 112 is pre-moistened with, for example, povidone-iodine USP 10%. In step 1506, the caregiver cleans the patient, by placing the nasal antiseptic swab into a first nostril of the patient, sweeping the first nasal antiseptic swab 112 around the first nostril.

In step 1508, the caregiver removes the second nasal antiseptic swab from the first cavity 106 and, in step 1510, opens the wrapper enveloping the second nasal antiseptic swab. The second nasal antiseptic swab may, preferably, also be premoistened with, for example, povidone-iodine USP 10%. In step 1512, following the instructions, the caregiver cleans the patient, by placing the second nasal antiseptic swab into a second nostril of the patient, sweeping the second nasal antiseptic swab around the second nostril.

In step 1514, the caregiver removes the third nasal antiseptic swab from the first cavity 106, and, in step 1516, opens the wrapper enveloping the third nasal antiseptic swab. The third nasal antiseptic swab may, preferably, also be premoistened with, for example, povidone-iodine USP 10%. In step 1518, following the instructions, the caregiver cleans the patient, by placing the third nasal antiseptic swab into the first nostril of the patient, sweeping the third nasal antiseptic swab around the first nostril.

In step 1520, the caregiver removes the fourth nasal antiseptic swab from the first cavity 106, and, in step 1522, opens the wrapper enveloping the fourth nasal antiseptic swab. The fourth nasal antiseptic swab may, preferably, also be premoistened with, for example, povidone-iodine USP 10%. In step 1524, following the instructions, the caregiver cleans the patient by placing the fourth nasal antiseptic swab into the second nostril of the patient, sweeping the fourth nasal antiseptic swab around the second nostril.

In step 1526, next, the caregiver removes the medicine cup 120 and the chlorhexidine gluconate bottle 114 from the second cavity 108 (or in case of the medicine cup 120 optionally from below the instructions panel 110). In step 1528, the caregiver then pours an amount of the chlorhexidine gluconate from the bottle 114 into the medicine cup 120. This amount may be all or less than all of the contents of the bottle 114 of chlorhexidine gluconate.

In step 1530, the caregiver then moistens the oral swab 116 in the chlorhexidine gluconate within the medicine cup 120 and, in step 1532, uses the oral swab 116 to cleanse the mouth (oral cavity) of the patient by sweeping the oral swab 116 across the gums and teeth of the patient.

In addition in step 1530, the caregiver moistens the toothbrush 118 in the chlorhexidine gluconate solution within the medicine cup 120 and, in step 1532, brushes the patient's teeth and gums with the toothbrush 118 moistened with the chlorhexidine gluconate.

Periodically during the cleansing of the gums with the oral swab 116 and the cleansing of the teeth and gums with toothbrush 118, the caregiver may re-moisten the oral swab 116 and/or the toothbrush 118 with the chlorhexidine gluconate from the medicine cup 120.

As needed, additional chlorhexidine gluconate may be added to the medicine cup 120 from the bottle 114 of chlorhexidine gluconate (provided the entire amount of the chlorhexidine is not transferred in the first instance into the medicine cup 120).

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A method of patient care comprising:
opening a package;
removing a first nasal swab from a first cavity defined by the package and an insert;
cleaning a first nostril of a patient with the first nasal swab;
removing a second nasal swab from the first cavity;
cleaning a second nostril of the patient with the second nasal swab;
removing a bottle of germicidal solution from the package;
removing an amount of the germicidal solution from the bottle of germicidal solution;
removing an oral swab from a second cavity defined by the package and the insert;
dispensing a portion of the germicidal solution onto the oral swab; and
cleaning a mouth of the patient with the oral swab.

2. The method of claim 1 further comprising:
removing a toothbrush from the second cavity defined by the package and the insert;
dispensing another portion of the germicidal solution onto the toothbrush;
cleaning the mouth of the patient with the toothbrush.

3. The method of claim 1 wherein said removing said amount of said germicidal solution comprises removing an amount of chlorohexidine gluconate.

4. The method of claim 1 further comprising:
removing a wrapper from the first nasal swab, wherein the first nasal swab is a premoistened nasal swab; and
removing another wrapper from said second nasal swab, wherein the second nasal swab is another premoistened nasal swab.

5. The method of claim 1 further comprising displaying printed instructions.

6. The method of claim 1 wherein said displaying said printed instructions further comprises displaying said printed instructions by removing a cover from the package when opening said package.

7. The method of claim 1 further comprising lifting said insert, wherein said lifting said insert raises a floor portion of the insert.

8. The method of claim 1 wherein said removing of said bottle of germicidal solution comprises removing said bottle of germicidal solution from a slot in said insert, wherein said slot secures said bottle of germicidal solution until said bottle of germicidal solution is removed.

\* \* \* \* \*